(12) United States Patent
Cleland et al.

(10) Patent No.: US 11,213,818 B2
(45) Date of Patent: Jan. 4, 2022

(54) SYSTEMS AND DEVICES FOR MICROFLUIDIC INSTRUMENTATION

(71) Applicant: SPECTRADYNE LLC, Rolling Hills Esate, CA (US)

(72) Inventors: Andrew N. Cleland, Chicago, IL (US); Jean-Luc Fraikin, Toronto (CA); Peter Meinhold, Santa Barbara, CA (US); Franklin Monzon, Rolling Hills Estates, CA (US)

(73) Assignee: Spectradyne LLC, Signal Hill, CA (US)

( * ) Notice: Subject to any disclaimer, the term of this patent is extended or adjusted under 35 U.S.C. 154(b) by 558 days.

(21) Appl. No.: 15/778,180

(22) PCT Filed: Nov. 22, 2016

(86) PCT No.: PCT/US2016/063411
§ 371 (c)(1),
(2) Date: May 23, 2018

(87) PCT Pub. No.: WO2017/091618
PCT Pub. Date: Jun. 1, 2017

(65) Prior Publication Data
US 2020/0298230 A1    Sep. 24, 2020

Related U.S. Application Data

(60) Provisional application No. 62/260,050, filed on Nov. 25, 2015.

(51) Int. Cl.
*B01L 3/00* (2006.01)
*B01L 9/00* (2006.01)
(Continued)

(52) U.S. Cl.
CPC .... *B01L 3/502715* (2013.01); *G01N 15/1056* (2013.01); *G01N 15/12* (2013.01);
(Continued)

(58) Field of Classification Search
CPC ......... B01L 3/502715; B01L 2200/025; B01L 2200/026; B01L 2200/027;
(Continued)

(56) References Cited

U.S. PATENT DOCUMENTS

2002/0119078 A1    8/2002    Jansa et al.
2006/0088443 A1*   4/2006    Mattila .............. G01N 35/0099
                                                         422/63
(Continued)

FOREIGN PATENT DOCUMENTS

WO    2013074693 A1    5/2013
WO    2013181285 A1    12/2013
WO    2014194556 A1    12/2014

*Primary Examiner* — Brian J. Sines
(74) *Attorney, Agent, or Firm* — Aura IP Law, PC

(57) ABSTRACT

Various embodiments herein disclose a device, comprising one or more fluid interfacing components and a cartridge holder, wherein the one or more fluid interfacing components are fixed while the cartridge holder moves along a linear guide. Also disclosed herein are methods of using the device to analyze a sample containing particles, and methods of diagnosing a disease in a subject by using the device.

33 Claims, 4 Drawing Sheets

(51) Int. Cl.
- *C12Q 1/00* (2006.01)
- *C12M 1/00* (2006.01)
- *C40B 60/00* (2006.01)
- *G01N 15/10* (2006.01)
- *G01N 15/12* (2006.01)
- *G01N 15/00* (2006.01)

(52) U.S. Cl.
CPC ... *B01L 2200/025* (2013.01); *B01L 2200/027* (2013.01); *B01L 2300/0645* (2013.01); *B01L 2400/0481* (2013.01); *B01L 2400/0487* (2013.01); *G01N 2015/0038* (2013.01); *G01N 2015/0065* (2013.01); *G01N 2015/1254* (2013.01)

(58) Field of Classification Search
CPC ........ B01L 2200/028; B01L 3/00; B01L 9/00; B01L 9/527; G01N 15/1056; G01N 2015/0065; G01N 2015/1254; G01N 21/01; G01N 27/07; G01N 27/30; G01N 33/5302; G01N 35/02; G01N 35/04; G01N 35/10; G01N 35/1081; C12Q 1/00; C12M 1/00; C40B 60/00; H01J 49/0409

See application file for complete search history.

(56) References Cited

U.S. PATENT DOCUMENTS

| | | | | |
|---|---|---|---|---|
| 2006/0289077 | A1* | 12/2006 | Klima, Jr. | B65B 3/12 141/9 |
| 2011/0207140 | A1* | 8/2011 | Handique | B01L 3/502723 435/6.12 |
| 2012/0190589 | A1* | 7/2012 | Anderson | G01F 23/02 506/39 |
| 2012/0195800 | A1* | 8/2012 | Clinton | G01N 33/5302 422/82.08 |
| 2016/0175840 | A1* | 6/2016 | Ingber | B01L 3/502715 422/502 |
| 2016/0187636 | A1* | 6/2016 | Ingber | G02B 21/14 348/79 |

* cited by examiner (A)

(B)

(A)

(B)

SYSTEMS AND DEVICES FOR MICROFLUIDIC INSTRUMENTATION

CROSS REFERENCE TO RELATED APPLICATIONS

This application is a National Phase of International Application No. PCT/US2016/063411, filed Nov. 22, 2016, which designated the U.S. and that International Application was published under PCT Article 21(2) in English. This application also includes a claim of priority under 35 U.S.C. § 119(e) to U.S. Provisional Application No. 62/260,050, filed Nov. 25, 2015, the entirety of which is hereby incorporated by reference.

FIELD OF THE INVENTION

The present invention relates generally to nanotechnology and, more particularly, to systems and devices for microfluidic instruments and analysis.

BACKGROUND

All publications herein are incorporated by reference to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

Applications of synthetic nanoparticles include cosmetics, photovoltaics and nanomedicine. Naturally occurring microparticles and nanoparticles mediate important physiological processes, and lethal viruses with diameters of about 50-150 nm kill millions of people annually. However, the practical development and use of micro- and nano-particles is significantly constrained by a lack of practical tools capable of detecting and characterizing particles in this size range. Thus, there is a need in the art for novel and effective methods and related instruments for nanoparticle analysis.

SUMMARY OF THE INVENTION

Various embodiments herein include a device comprising one or more fluid interfacing components, and a cartridge holder, wherein the one or more fluid interfacing components are fixed while the cartridge holder moves along a linear guide. In another embodiment, the device further comprises a cartridge in the cartridge holder. In another embodiment, the cartridge is reversibly engaged with one or more fluid interfacing components. In another embodiment, the device further comprises a pressure supply wherein the pressure supply controls the flow of fluid through different parts of the cartridge. In another embodiment, the cartridge comprises one or more electrodes. In another embodiment, the cartridge comprises electrodes that detect electrical signals generated when particles pass through a constriction in the cartridge. In another embodiment, the constriction is a nano-sized constriction. In another embodiment, the fluid interfacing components comprise one or more tubes. In another embodiment, the one or more tubes insert into a cartridge provided in the cartridge holder. In another embodiment, the one or more of the fluid interfacing components does not make direct contact with fluid in a cartridge provided in the cartridge holder. In another embodiment, the cartridge holder provides means for making one or more electrical contacts to a cartridge provided in the cartridge holder. In another embodiment, the device further comprises a locking system to avoid emission of fluid and/or gas when fluid and/or gas tubes are not engaged by a cartridge provided in the cartridge holder. In another embodiment, the device further comprises one or more of bias voltage contacts and one or more sense voltage contacts. In another embodiment, the device further comprises use of electrical signaling to detect proper operation of the device. In another embodiment, the device is a handheld device.

Other embodiments include a method of analyzing a sample, comprising providing a device comprising one or more fluid interfacing components and a cartridge holder, wherein the one or more fluid interfacing components are fixed while the cartridge moves along a linear guide, and using the device to analyze the sample. In another embodiment, the method further comprises a cartridge in the cartridge holder. In another embodiment, the cartridge is reversibly engaged with one or more fluid interfacing components. In another embodiment, the cartridge comprises electrodes. In another embodiment, the electrodes detect electrical signals generated when particles pass through a constriction in the cartridge. In another embodiment, the method further comprises a pressure supply wherein the pressure supply controls the flow of fluid through different parts of the cartridge. In another embodiment, the sample comprises micro-particles and/or nano-particles. In another embodiment, the one or more fluid interfacing components comprise a plurality of tubes. In another embodiment, the one or more of the fluid interfacing components does not make direct contact with fluid in a cartridge provided in the cartridge holder. In another embodiment, the device provides a means for making electrical contact to a cartridge provided in the cartridge holder. In another embodiment, the method further comprises use of a locking system to avoid emission of fluid and/or gas when fluid and/or gas tubes are not engaged by a cartridge provided in the cartridge holder. In another embodiment, the method further comprises use of one or more of bias voltage contacts and one or more sense voltage contacts. In another embodiment, the method further comprises use of electrical signaling to detect proper operation of the device. In another embodiment, the sample is a biological sample. In another embodiment, the biological sample includes virus and/or bacterium particles. In another embodiment, the sample comprises one or more particles.

Other embodiments include a method of diagnosing a disease in a subject, comprising: obtaining a sample from the subject, providing a device comprising one or more fluid interfacing components, and a cartridge holder, wherein the one or more fluid interfacing components are fixed while the cartridge holder moves along a linear guide, using the device to analyze the sample and determine the presence or absence of one or more markers associated with a disease, and diagnosing the disease in the subject based on the presence of the one or more markers. In another embodiment, the marker is a biomarker. In another embodiment, the sample is a biological sample. In another embodiment, the subject is human. In another embodiment, the subject is a rodent.

Other features and advantages of the invention will become apparent from the following detailed description, taken in conjunction with the accompanying drawings, which illustrate, by way of example, various embodiments of the invention.

BRIEF DESCRIPTION OF THE FIGURES

Exemplary embodiments are illustrated in referenced figures. It is intended that the embodiments and figures disclosed herein are to be considered illustrative rather than restrictive.

DESCRIPTION OF THE INVENTION

Figure 1:
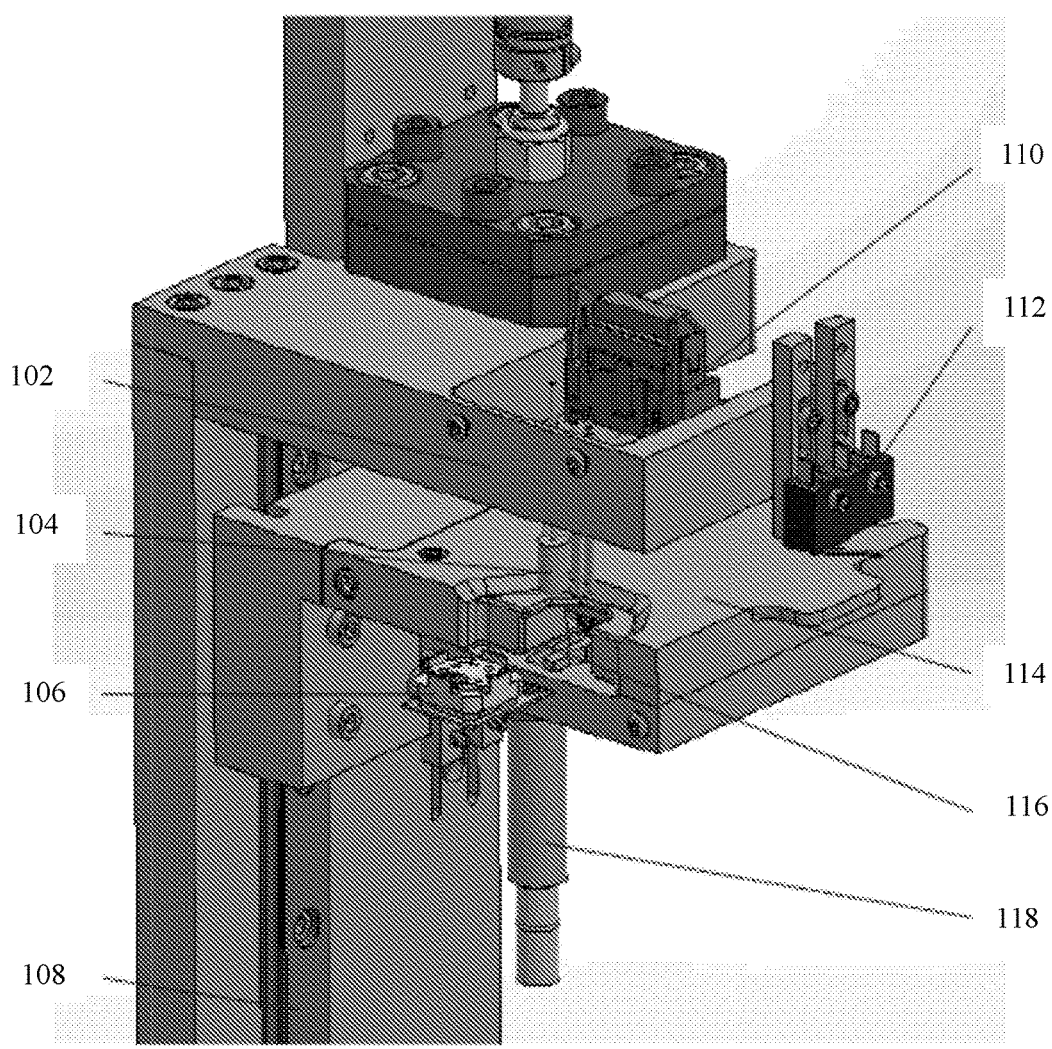
FIG. 1 depicts, in accordance with embodiments herein, an example of a microfluidic device described herein.
Figure 2:
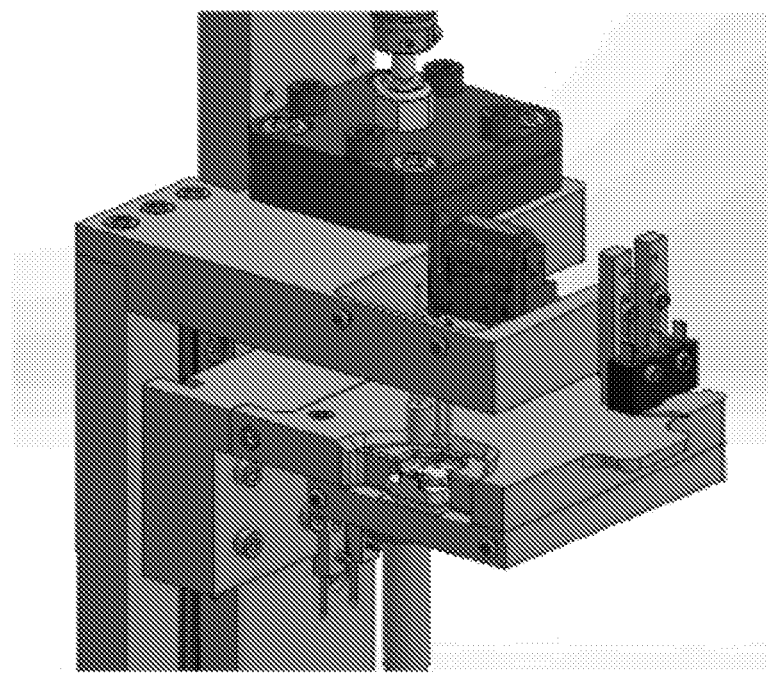
FIG. 2 depicts, in accordance with embodiments herein, an example of a microfluidic device described herein.
Figure 2:
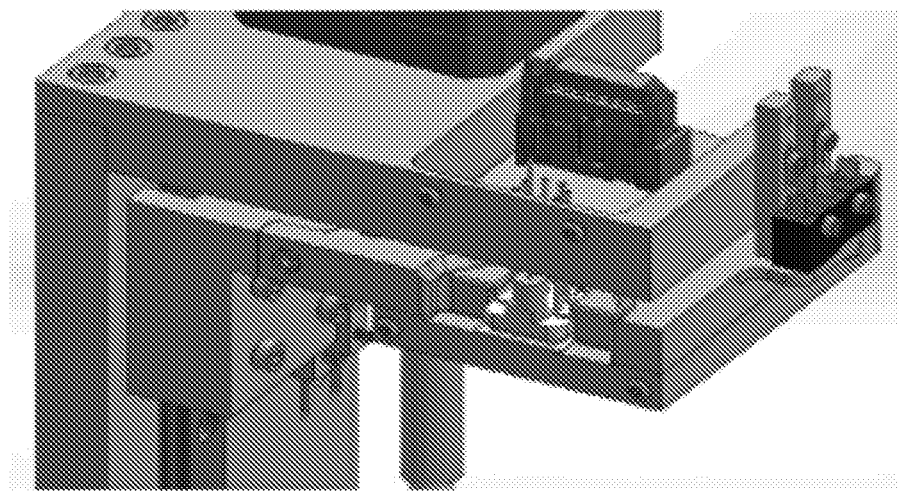
Figure 3:
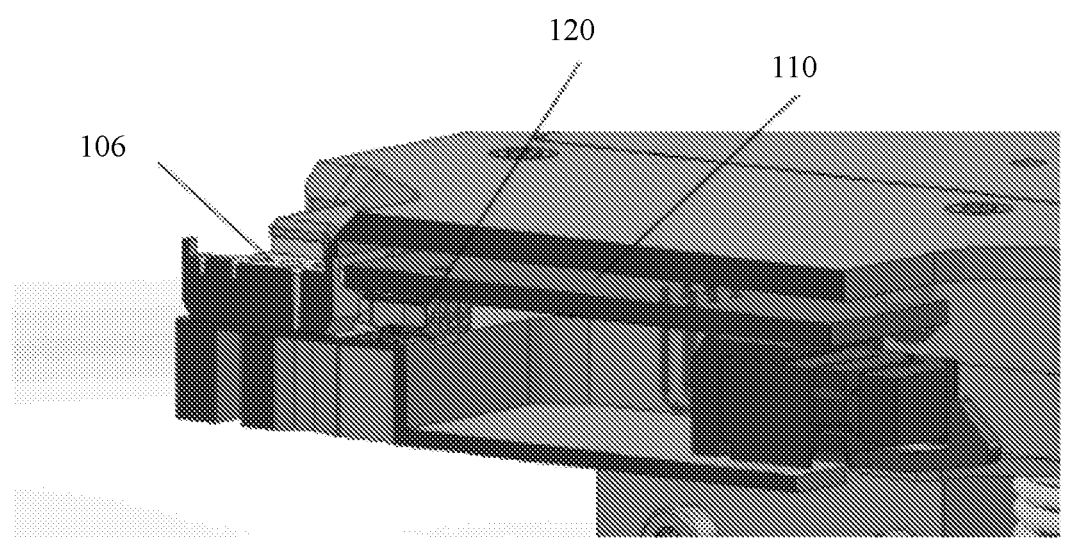
FIG. 3 depicts, in accordance with embodiments herein, an example of a microfluidic device described herein.
Figure 4:
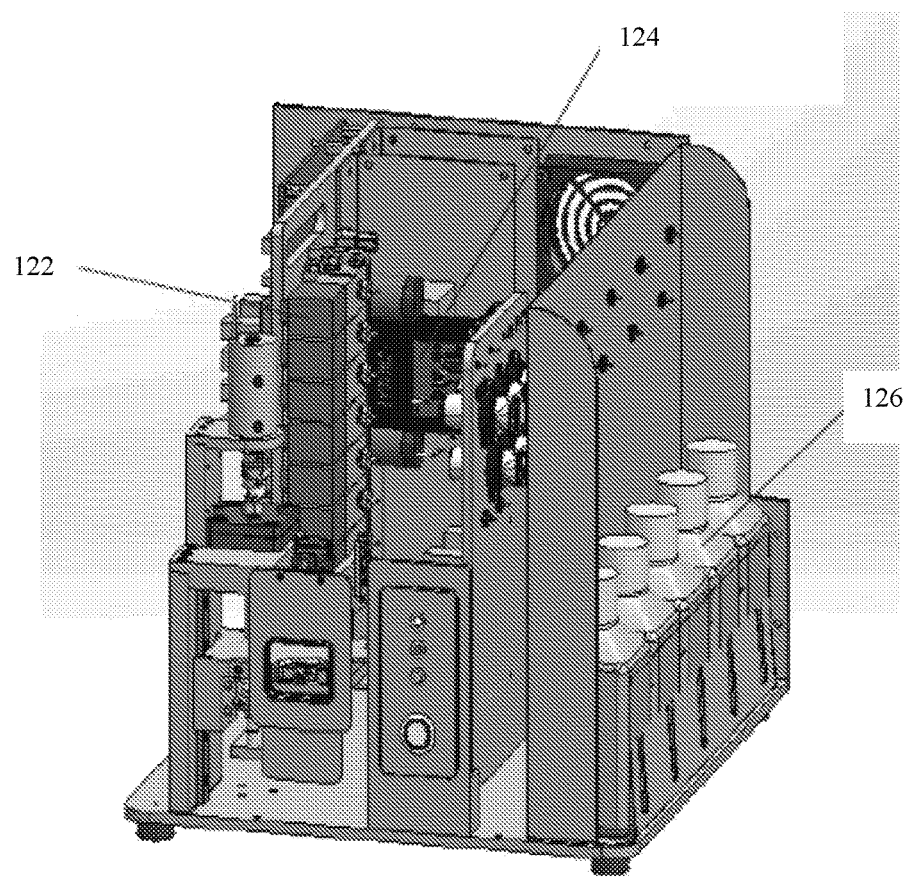
FIG. 4 depicts, in accordance with embodiments herein, an example of a microfluidic device described herein.
Figure 4:
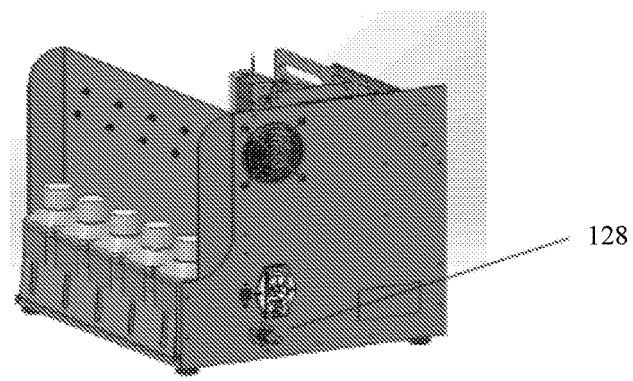

All references cited herein are incorporated by reference in their entirety as though fully set forth. Unless defined otherwise, technical and scientific terms used herein have the same meaning as commonly understood by one of ordinary skill in the art to which this invention belongs. Hornyak, et al., Introduction to Nanoscience and Nanotechnology, CRC Press (2008); Singleton et al., Dictionary of Microbiology and Molecular Biology 3rd ed., J. Wiley & Sons (New York, N.Y. 2001); March, Advanced Organic Chemistry Reactions, Mechanisms and Structure 7th ed., J. Wiley & Sons (New York, N.Y. 2013); and Sambrook and Russel, Molecular Cloning: A Laboratory Manual 4th ed., Cold Spring Harbor Laboratory Press (Cold Spring Harbor, N.Y. 2012), provide one skilled in the art with a general guide to many of the terms used in the present application. One skilled in the art will recognize many methods and materials similar or equivalent to those described herein, which could be used in the practice of the present invention. Indeed, the present invention is in no way limited to the methods and materials described.

As disclosed herein, the inventors developed various microfluidic instruments and related methods that may be used in conjunction with nanotechnology and nanoparticle analysis. For example, in one embodiment, the present disclosure provides a device, comprising one or more fluid interfacing components 102; and a cartridge holder 114, wherein the one or more fluid interfacing components are fixed while the cartridge holder moves along a linear guide. In one embodiment, the cartridge holder 114 further comprises a cartridge 106. In one embodiment, the cartridge 106 is reversibly engaged with one or more fluid interfacing components 102. In one embodiment, the device further comprises a pressure supply 124 wherein the pressure supply controls the flow of fluid through different parts of the cartridge. In one embodiment, the cartridge comprises electrodes and wherein the electrodes detect electrical signals generated when particles pass through a constriction in the cartridge. In one embodiment, the constriction is a micro- or nano-sized constriction. In one embodiment, the fluid interfacing components 102 comprise tubes 104. In one embodiment, the tubes 104 insert into a cartridge 106 provided in the cartridge holder 114. In one embodiment, the one or more fluid interfacing components 102 does not make direct contact with fluid in a cartridge 106 provided in the cartridge holder 114. In one embodiment, the cartridge holder 114 provides means for making one or more electrical contacts to a cartridge 106 provided in the cartridge holder. In one embodiment, the device further comprises a locking system to avoid emission of fluid and/or gas when fluid and/or gas tubes are not engaged by a cartridge provided in the cartridge holder. In one embodiment, the device further comprises a pair or more of bias voltage contacts and one or more sense voltage contacts. In one embodiment, the device further comprises use of electrical signaling to detect proper operation of the device. In one embodiment, the device is a handheld device.

In another embodiment, the present disclosure provides a method of analyzing a sample containing particles, comprising providing a device comprising one or more fluid interfacing components 102 and a cartridge holder 114, wherein the one or more fluid interfacing components are fixed while the cartridge moves along a linear guide, and using the device to analyze the sample. In one embodiment, the method further comprises a cartridge 106 in the cartridge holder 114. In one embodiment, the cartridge 106 is reversibly engaged with one or more fluid interfacing components 102. In one embodiment, the particles are micro-particles or nano-particles. In one embodiment, the cartridge comprises electrodes and wherein the electrodes detect electrical signals generated when particles pass through a constriction in the cartridge. In one embodiment, the method further comprises a pressure supply wherein the pressure supply controls the flow of fluid through different parts of the cartridge. In another embodiment, the pressure supply is managed by components comprising a pressure maintaining unit 124, pressurized volume 126, and pressure supply input 128. In one embodiment, the fluid interfacing components 102 comprise tubes 104. In one embodiment, one or more of the fluid interfacing components 102 does not make direct contact with fluid in a cartridge 106 provided in the cartridge holder 114. In one embodiment, the device provides means for making electrical contact to a cartridge provided in the cartridge holder. In one embodiment, the device further comprises a locking system to avoid emission of fluid and/or gas when fluid and/or gas tubes are not engaged by a cartridge provided in the cartridge holder 114. In one embodiment, the device further comprises a pair or more of bias voltage contacts and one or more sense voltage contacts. In one embodiment, the method further comprises use of electrical signaling to detect proper operation of the device. In one embodiment, the sample is a biological sample comprising one or more particles. In one embodiment, the particle is a virus or a bacterium.

In another embodiment, the present disclosure provides a method of diagnosing a disease in a subject, comprising: obtaining a sample from the subject; providing a device comprising one or more fluid interfacing components 102; and a cartridge holder 114, wherein the one or more fluid interfacing components 102 are fixed while the cartridge holder 114 moves along a linear guide; using the device to analyze the sample and determine the presence or absence of one or more markers associated with the disease; and diagnosing the disease in the subject based on the presence of the one or more markers. In one embodiment, the marker is a biomarker. In one embodiment, the sample is a biological sample.

In one embodiment, the device provided in the present disclosure comprises a fluid interfacing component 102 and a cartridge holder 114, and wherein the fluid interfacing component 102 is fixed while the cartridge holder moves along a linear guide, to reversibly engage the cartridge 106 with the fluid interfacing components. In another embodiment, the fluid interface components comprise tubes 104 that insert into the cartridge 106 when the cartridge 106 is engaged by the cartridge holder 114. In another embodiment, the tubes of the fluid interface components are fabricated of conductive material and can provide electrical contact to the fluid entering the cartridge as well as the fluid inside the cartridge. In another embodiment the tubes fabricated of conductive material are electrically connected to a circuit board that is connected to a microprocessor. In another embodiment, the tubes fabricated of conductive material may be fixed to a circuit board or other rigid component relative to the cartridge holder. In another embodiment, electrical connections to the tubes may be used to measure currents in the fluid or voltages of the tubes in contact with the fluid, or to apply currents or voltages to the fluid. In another embodiment, the fluid interface components 102 may also provide shielding to reduce electrical noise from the environment interfering with the electrical measurements, or operation of the cartridge or fluid system.

Further, in another embodiment, the fluid interfacing components 102 provide a means for transporting fluid to, within and out of the cartridge 106. In one embodiment, gas pressure is used to move the fluid in the cartridge. In another embodiment, the fluid interfacing components do not make direct contact with the fluid in the cartridge, so as to minimize or eliminate contamination of the fluid interface components 102 by contacting the fluid, and to minimize or eliminate the need to clean the fluid interfacing components 102. In another embodiment, the fluid interfacing components 102 comprise a tube 104 that is wider than the opening of a reservoir in the cartridge that makes a seal when pressed onto the cartridge in order to apply gas pressure to the reservoir and move fluid from inside the reservoir to other areas in the cartridge without directly contacting the fluid. In one embodiment a tube 104 that is wider than the opening of a reservoir in the cartridge 106 engages with a sealing ring patterned into the cartridge in order to provide a seal. In one embodiment, the device further comprises a lead screw 118.

In another embodiment, the fluid interfacing components 102 provide interfacing between only one fluid volume and the cartridge 106. In another embodiment, the fluid interfacing components 102 provide interfacing between more than one fluid volume and the cartridge 106. In another embodiment, the fluid interface components 102 are rigid, to overcome difficulties in the field arising from flexible fluid interfaces, such as weak or leaky fluid interface, or aligning flexible fluid interfaces with appropriate connections in a cartridge.

In another embodiment, the cartridge holder 114 also provides means for making electrical contact to the cartridge 106. In one embodiment, the means for electrical contact comprise a spring connector 120 on a circuit board 110 with other circuitry, the circuit board 110 is mounted onto the cartridge holder 114, and the cartridge 106 slides into the cartridge holder 114 in such a way as for electrical contacts on the cartridge 106 to connect with the spring connector 120. For example, the circuit board 110 and spring connector 120 may be connected to a microprocessor and used to measure voltages or currents in the cartridge 106 or to apply currents or voltages to the cartridge 106. In another embodiment, the cartridge holder 114 also may provide means for electrical shielding to reduce electrical noise from the environment interfering with the electrical measurements or operation of the cartridge 106 or fluid system.

In another embodiment, the cartridge holder 114 is made of three pieces of metal, possibly including a slot 116 in which the cartridge 106 is placed, providing a substantially enclosed volume to provide shielding from electrical noise. In another embodiment, the circuit board 110 can be attached to the cartridge holder 114 allowing a spring contact 120 mounted to the circuit board 110 to press against electrical contacts on the cartridge 106 when the cartridge is inserted, thereby providing electrical contact between the circuit board 110 and cartridge 106. In another embodiment, the cartridge holder 114 slides along a linear rail 108 such that when the cartridge holder is in an upper position the tubes of the fluid interface components engage with ports on the cartridge. In another embodiment, the fluid interface components 102 comprise a number of separate tubes that make individual electrical, fluidic and pneumatic contact with fluids in the cartridge and possibly one or more tubes that do not make direct contact with fluids in the cartridge but provide gas pressure connections to move fluids inside the cartridge.

In another embodiment, the present invention provides a method of locking the device to avoid emission of fluid or gas when the fluid and gas nozzles are not engaged in the cartridge 106. For example, two requirements for safe operation include that a valid cartridge 106 is engaged with the preamplifier circuit, and the fluid and gas connectors are sealed to the cartridge 106. The first requirement assures that when electrical contact is confirmed between the preamplifier connector and the contacts on the cartridge 106, the cartridge 106 is in the proper position for insertion of the fluid and gas control nozzles. In accordance with various embodiments herein, sensing of this connection is done by measuring the current between two contacts on the cartridge 106, connected via a fusible link which is part of the metal circuit patterned on the glass component of the cartridge 106. A second requirement is that the cartridge 106 be raised so that the fluid and gas control nozzles make a leak-tight seal at the cartridge ports. In accordance with various embodiments herein, this is done by sensing the state of an electromechanical limit switch 112, whose position is adjusted to ensure there is a gas tight seal when the switch is engaged.

In another embodiment, the present invention provides a bias voltage and sensing method. In one embodiment, the microfluidic cartridge 106 used in conjunction with the instrument requires a pair of bias voltage contacts and a sense voltage contact for proper operation and for detection of particles flowing through the nano- or micro-constriction. In one implementation, the bias voltage is applied and the sense voltage detected through metal tubes that make contact with the fluid that fills the microfluidic volumes in the cartridge 106. In another implementation, the bias voltage is applied and the sense voltage detected through metal wires submerged in the same fluid. In another implementation, the bias voltage is applied and the sense voltage detected through metal electrodes patterned on the microfluidic cartridge 106, with mechanical contacts made between the instrument and the cartridge 106. In another implementation, some combination of these various methods are used for applying the bias voltage and the detecting the sense voltage. The bias voltage is provided by an electrical circuit that allows adjusting the bias voltage to whatever value is desired, and this bias voltage can be sensed in order to maintain the proper value. In another embodiment, the sense voltage is measured using an electrical circuit that returns analog or digitally encoded values for the detected voltage as a function of time.

In another embodiment, the present invention provides a fluid detection method and/or device. For example, one difficulty in operating microfluidic systems without a method to view the operation under a microscope is knowing whether the microfluidic device has been properly filled with fluid, a critical part of successfully operating such devices. In accordance with various embodiments herein, in one embodiment, the present invention provides a technique involving the use of electrical signaling to detect proper filling of the device, which relies on using a microfluidic device fabricated with non-conducting materials (such as glass and insulating organic polymers), while using fluids that at least weakly conduct electricity (typically by including some form of ions in the fluid, such as disassociated salts). In another embodiment, the present invention provides a means of applying constant or time-varying voltage to various parts of the device, in one embodiment by making electrical contact to the fluid using conducting wires, in another embodiment by making electrical contact to the fluid using metal tubes that are also used to transport fluid to and/or from the microfluidic device. The constant or time-varying voltages cause electrical currents to flow through the fluid in the device, and by monitoring such currents and in particular monitoring their detailed time-varying behavior, the proper filling of various parts of the microfluidic device can be positively verified. For example, in one embodiment voltages are applied that oscillate at different frequencies, and by detecting the frequencies of the resulting currents, separate and independent verifications of proper filling of different parts of the device can be made. In another embodiment constant or time-varying currents are applied, and the voltages resulting from these are monitored; in another embodiment some combination of voltage or current biases are applied and currents and voltages resulting from these are detected.

In another embodiment, the present invention provides a pressure maintaining unit 124 for pressure application and/or control. For example, microfluidic cartridges used in conjunction with this instrument typically have fluid flow that is controlled by gas pressure provided by the instrument, either an external source of pressurized gas or using a small compressor. In one embodiment, in order to simplify the instrument, only one pressure supply is used for the instrument. In another embodiment, this gas pressure is used at various points in the instrument to control flow through different parts of the cartridge 106, and proper operation of the cartridge 106 requires that different points have different gas pressures, even though the supply is only at a single fixed pressure. In one embodiment, these various pressures are provided by different, independent electronically-controlled pressure maintaining units 124, thus directly controlling the pressure at each point in the instrument. In a different embodiment, different pressures are provided by including in the instrument separate pressurized volumes 126 that are separately pressurized by a one or more electronically-controlled pressure maintaining units 124. As these volumes are less expensive to produce and maintain than the pressure maintaining units, this provides a significant cost saving in the production of the instrument. Each pressurized volume 126 thus included has a certain target pressure setting, and the one (or more) pressure maintaining unit(s) 124 is (are) periodically connected to the pressurized volume 126 in order to measure and possibly adjust the pressure in that volume, separate from the other volumes. In an embodiment, electronically-controlled valves 122 may be used to connect and/or disconnect the pressurized volumes 126 from the one or more pressure maintaining units 124. In an embodiment, electronically-controlled valves 122 may be used to connect and/or disconnect the pressurized volumes 126 from fluid in the cartridge 106.

In another embodiment, the present disclosure provides bias electrodes in tubing. For example, an important part of operating the instrument in conjunction with the microfluidic cartridge is a method to apply and sense electrical voltages and currents to various parts of the cartridge. In one embodiment, these voltages and currents are applied and sensed by making electrical contact to electrodes patterned on the cartridge, to which mechanical contacts are made when loading the cartridge 106 into the instrument. In another embodiment these voltages and currents are applied and sensed by including in the instrument wires that are submerged in fluid that is continuous through to the microfluidic volumes in the cartridge 106. In another embodiment these voltages and currents are applied and sensed by including in the instrument metallic tubes 104 that enclose fluid that is continuous through to the microfluidic volumes in the cartridge 106. In another embodiment, some combination of one or more of these methods is used to make electrical contact to the fluid.

In another embodiment, the present disclosure provides a device with neutral bias at the sense electrode to prevent corrosion. For example, in one embodiment, the microfluidic cartridge 106 that is an integral part of the operation of the instrument includes various patterned electrodes, one or more of which is used to detect the electrical signals generated when particles pass through the nanoconstriction(s) in the cartridge 106. These electrodes are typically thin films of metal that can corrode when in contact with a conducting fluid that has an electrical potential sufficiently above or below the potential of the electrode. In one embodiment of the instrument, the inventors provide electrical circuitry that monitors the amount of current flowing through this electrode, and adjusts the electrical potential of the fluid or the electrode in order to minimize this electrical current and thus prevent the corrosion. In another embodiment, the electrical connection to these electrode(s) is only through a capacitor. This, for example, provides no galvanic connection between that electrode and any other conducting path, so that the electrode self-biases to a potential very close to that of the fluid in contact with the electrode, thus automatically stopping any corrosive effects.

Various embodiments herein describe microfluidic instruments and devices, as well as method of preparing and use thereof, that may be used to analyze and/or modify biological samples including samples comprising one or more micro particles or nanoparticles. As readily apparent to one of skill in the art, any number of methods that involve analysis of nanoparticle or biological samples may be used in conjunction with various embodiments described herein, and the disclosure may also include methods of diagnosis, prognosis and/or treatment of a disease or condition in a subject. For example, in one embodiment, the present disclosure provides a method of diagnosing cancer in a subject by obtaining a sample from a subject, and then using a device, comprising one or more fluid interfacing components 102 and a cartridge holder 114 wherein the one or more fluid interfacing components 102 are fixed while the cartridge holder 114 moves along a linear guide, and using the device analyze the biological sample to determine the presence or absence of one or more biomarkers associated with susceptibility to cancer, and diagnosing susceptibility to cancer based on the presence of one or more biomarkers.

The various methods and techniques described above provide a number of ways to carry out the invention. Of course, it is to be understood that not necessarily all objectives or advantages described may be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as may be taught or suggested herein. A variety of advantageous and disadvantageous alternatives are mentioned herein. It is to be understood that some preferred embodiments specifically include one, another, or several advantageous features, while others specifically exclude one, another, or several disadvantageous features, while still others specifically mitigate a present disadvantageous feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be mixed and matched by one of ordinary skill in this art to perform methods in accordance with principles described herein. Among the various elements, features, and steps some will be specifically included and others specifically excluded in diverse embodiments.

Although the invention has been disclosed in the context of certain embodiments and examples, it will be understood by those skilled in the art that the embodiments of the invention extend beyond the specifically disclosed embodiments to other alternative embodiments and/or uses and modifications and equivalents thereof.

Many variations and alternative elements have been disclosed in embodiments of the present invention. Still further variations and alternate elements will be apparent to one of skill in the art. Among these variations, without limitation, are the selection of constituent modules for the inventive compositions, and the diseases and other clinical conditions that may be diagnosed, prognosed or treated therewith. Various embodiments of the invention can specifically include or exclude any of these variations or elements.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

In some embodiments, the terms "a" and "an" and "the" and similar references used in the context of describing a particular embodiment of the invention (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Preferred embodiments of this invention are described herein, including the best mode known to the inventors for carrying out the invention. Variations on those preferred embodiments will become apparent to those of ordinary skill in the art upon reading the foregoing description. It is contemplated that skilled artisans can employ such variations as appropriate, and the invention can be practiced otherwise than specifically described herein. Accordingly, many embodiments of this invention include all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above cited references and printed publications are herein individually incorporated by reference in their entirety.

In closing, it is to be understood that the embodiments disclosed herein are illustrative of the principles of the present invention. Other modifications that can be employed can be within the scope of the invention. Thus, by way of example, but not of limitation, alternative configurations of the present invention can be utilized in accordance with the teachings herein. Accordingly, embodiments of the present invention are not limited to that precisely as shown and described.

EXAMPLES

The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention.

Example 1

Cartridge Interface and Loading Mechanism—Generally

A disposable cartridge 106 is inserted into the instrument's cartridge holder 114, which provides alignment between the cartridge 106 and the fluid interfacing components 102 in the instrument. The fluid interfacing components 102 are held fixed while the cartridge holder 114 moves along a linear guide, to reversibly engage the cartridge 106 with the fluid interfacing components 102. In one embodiment, the fluid interface components 102 comprise tubes 104 that insert into the cartridge 106 when the cartridge 106 is engaged by the cartridge holder 114. In another embodiment the tubes 104 of the fluid interface components 102 are fabricated of conductive material and can provide electrical contact to the fluid entering the cartridge 106 as well as the fluid inside the cartridge 106. In another embodiment the tubes 104 fabricated of conductive material are electrically connected to a circuit board that is connected to a microprocessor. The tubes 104 fabricated of conductive material may be fixed to a circuit board or other rigid component relative to the cartridge holder 114. Electrical connections to the tubes 104 may be used to measure currents in the fluid or voltages of the tubes 104 in contact with the fluid, or to apply currents or voltages to the fluid. The fluid interface components 102 may also provide shielding to reduce electrical noise from the environment interfering with the electrical measurements or operation of the cartridge 106 or fluid system.

The fluid interfacing components provide a means for transporting fluid to, within and out of the cartridge 106. In one embodiment gas pressure is used to move the fluid in the cartridge 106. In one embodiment the fluid interfacing components 102 do not make direct contact with the fluid in the cartridge 106, so as to minimize or eliminate contamination of the fluid interface components by contacting the fluid, and to minimize or eliminate the need to clean the fluid interfacing components. In one embodiment, the fluid interfacing components 102 comprise a tube 104 that is wider than the opening of a reservoir in the cartridge 106 that makes a seal when pressed onto the cartridge 106 in order to apply gas pressure to the reservoir and move fluid from inside the reservoir to other areas in the cartridge 106 without directly contacting the fluid. In one embodiment a tube 104 that is wider than the opening of a reservoir in the cartridge 106 engages with a sealing ring patterned into the cartridge 106 in order to provide a seal.

In one embodiment the fluid interfacing components 102 provide interfacing between only one fluid volume and the cartridge 106. In another embodiment the fluid interfacing components 102 provide interfacing between more than one fluid volume and the cartridge 106. In one embodiment the fluid interface components 102 are rigid, to overcome difficulties in the prior art arising from flexible fluid interfaces, such as weak or leaky fluid interface, or aligning flexible fluid interfaces 102 with appropriate connections in a cartridge 106.

The cartridge holder also provides means for making electrical contact to the cartridge 106 itself. In one embodiment the means for electrical contact comprise a spring connector 120 on a circuit board 110 with other circuitry, the circuit board 110 is mounted onto the cartridge holder 114, and the cartridge 106 slides into the cartridge holder 114 in such a way as for electrical contacts on the cartridge 106 to connect with the spring connector 120. The circuit board 110 and spring connector 120 may be connected to a microprocessor and used to measure voltages or currents in the cartridge 106 or to apply currents or voltages to the cartridge 106. The cartridge holder 114 also may provide means for electrical shielding to reduce electrical noise from the environment interfering with the electrical measurements or operation of the cartridge 106 or fluid system.

In one embodiment the cartridge holder 114 is made of three pieces of metal, possibly including a slot 116 in which the cartridge 106 is placed, providing a substantially enclosed volume to provide shielding from electrical noise. The circuit board can be attached to the cartridge holder allowing a spring contact mounted to the circuit board to press against electrical contacts on the cartridge 106 when the cartridge 106 is inserted, thereby providing electrical contact between the circuit board and cartridge 106. The cartridge holder 114 slides along a linear rail 108 such that when the cartridge holder 114 is in an upper position the tubes 104 of the fluid interface components 102 engage with ports on the cartridge 106. The fluid interface components 102 comprise a number of separate tubes 104 that make individual electrical, fluidic and pneumatic contact with fluids in the cartridge 106 and possibly one or more tubes 104 that do not make direct contact with fluids in the cartridge 106 but provide gas pressure connections to move fluids inside the cartridge 106.

Example 2

A Method for 'Locking' the System to Avoid Emission of Fluid or Gas when the Fluid and Gas Nozzles are not Engaged in the Cartridge Two requirements for safe operation are that a valid cartridge is engaged with the preamplifier circuit and the fluid and gas connectors are sealed to the cartridge. The first requirement assures that when electrical contact is confirmed between the preamplifier connector and the contacts on the cartridge, the cartridge is in the proper position for insertion of the fluid and gas control nozzles. Sensing of this connection is done by measuring the current between two contacts on the cartridge, connected via a fusible link which is part of the metal circuit patterned on the glass component of the cartridge. A second requirement is that the cartridge be raised so that the fluid and gas control nozzles make a leak-tight seal at the cartridge ports. This is done by sensing the state of an electromechanical limit switch 112, whose position is adjusted to ensure there is a gas tight seal when the switch is engaged.

Example 3

Bias Voltage and Sensing Method

The microfluidic cartridge used in conjunction with the instrument requires a pair of bias voltage contacts and a sense voltage contact for proper operation and for detection of particles flowing through the nano- or micro-constriction. In one implementation the bias voltage is applied and the sense voltage detected through metal tubes that make contact with the fluid that fills the microfluidic volumes in the cartridge. In another implementation the bias voltage is applied and the sense voltage detected through metal wires submerged in the same fluid. In a third implementation the bias voltage is applied and the sense voltage detected through metal electrodes patterned on the microfluidic cartridge, with mechanical contacts made between the instrument and the cartridge. In a fourth implementation some combination of these various methods are used for applying the bias voltage and the detecting the sense voltage. The bias voltage is provided by an electrical circuit that allows adjusting the bias voltage to whatever value is desired, and this bias voltage can be sensed in order to maintain the proper value. The sense voltage is measured using an electrical circuit that returns analog or digitally encoded values for the detected voltage as a function of time.

Example 4

The Fluid Detect Method

One difficulty in operating microfluidic systems without a method to view the operation under a microscope is knowing whether the microfluidic device has been properly filled with fluid, a critical part of successfully operating such devices. Here we claim a technique involving the use of electrical signaling to detect proper filling of the device, which relies on using a microfluidic device fabricated with non-conducting materials (such as glass and insulating organic polymers), while using fluids that at least weakly conduct electricity (typically by including some form of ions in the fluid, such as disassociated salts). Included in the design of the instrument are various methods for applying constant or time-varying voltage to various parts of the device, in one embodiment by making electrical contact to the fluid using conducting wires, in another embodiment by making electrical contact to the fluid using metal tubes that are also used to transport fluid to and/or from the microfluidic device. The constant or time-varying voltages cause electrical currents to flow through the fluid in the device, and by monitoring such currents and in particular monitoring their detailed time-varying behavior, the proper filling of various parts of the microfluidic device can be positively verified. For example, in one embodiment voltages are applied that oscillate at different frequencies, and by detecting the frequencies of the resulting currents, separate and independent verifications of proper filling of different parts of the device can be made. In another embodiment constant or time-varying currents are applied, and the voltages resulting from these are monitored; in another embodiment some combination of voltage or current biases are applied and currents and voltages resulting from these are detected.

Example 5

The Pressure Application and Control

The microfluidic cartridges used in conjunction with this instrument typically have fluid flow that is controlled by gas pressure provided by the instrument, either an external source of pressurized gas or using a small compressor. In order to simplify the instrument, only one pressure supply is used for the instrument. This gas pressure is used at various points in the instrument to control flow through different parts of the cartridge, and proper operation of the cartridge requires that different points have different gas pressures, even though the supply is only at a single fixed pressure. In one embodiment, these various pressures are provided by different, independent electronically-controlled pressure maintaining units, thus directly controlling the pressure at each point in the instrument. In a different embodiment, different pressures are provided by including in the instrument separate volumes that are separately pressurized by a one or more electronically-controlled pressure maintaining units. As these volumes are less expensive to produce and maintain than the pressure maintaining units, this provides a significant cost saving in the production of the instrument. Each volume thus included has a certain target pressure setting, and the one (or more) pressure maintaining unit(s) is (are) periodically connected to the volume in order to measure and possibly adjust the pressure in that volume, separate from the other volumes. Electronically-controlled valves are used to connect and disconnect the volumes from the pressure maintaining unit, and to connect and disconnect the volumes from fluid in the cartridge.

Example 6

Using Bias Electrodes in the Tubing, (Using the Electrodes Themselves as Tubes would be One Embodiment)

In one embodiment, one aspect of operating the instrument in conjunction with the microfluidic cartridge is a method to apply and sense electrical voltages and currents to various parts of the cartridge. In one embodiment, these voltages and currents are applied and sensed by making electrical contact to electrodes patterned on the cartridge, to which mechanical contacts are made when loading the cartridge into the instrument. In another embodiment these voltages and currents are applied and sensed by including in the instrument wires that are submerged in fluid that is continuous through to the microfluidic volumes in the cartridge. In another embodiment these voltages and currents are applied and sensed by including in the instrument metallic tubes that enclose fluid that is continuous through to the microfluidic volumes in the cartridge. In another embodiment, some combination of one or more of these methods is used to make electrical contact to the fluid.

Example 7

Keeping Neutral Bias at the Sense Electrode to Prevent Corrosion

The microfluidic cartridge that is an integral part of the operation of the instrument includes various patterned electrodes, one or more of which is used to detect the electrical signals generated when particles pass through the nanoconstriction(s) in the cartridge. These electrodes are typically thin films of metal that can corrode when in contact with a conducting fluid that has an electrical potential sufficiently above or below the potential of the electrode. In one embodiment of the instrument, we include electrical circuitry that monitors the amount of current flowing through this electrode, and adjusts the electrical potential of the fluid or the electrode in order to minimize this electrical current and thus prevent the corrosion. In another embodiment, the electrical connection to these electrode(s) is only through a capacitor, in other words there is no galvanic connection between that electrode and any other conducting path, so that the electrode self-biases to a potential very close to that of the fluid in contact with the electrode, thus automatically stopping any corrosive effects.

Various embodiments of the invention are described above in the Detailed Description. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventors that the words and phrases in the specification and claims be given the ordinary and accustomed meanings to those of ordinary skill in the applicable art(s).

The foregoing description of various embodiments of the invention known to the applicant at this time of filing the application has been presented and is intended for the purposes of illustration and description. The present description is not intended to be exhaustive nor limit the invention to the precise form disclosed and many modifications and variations are possible in the light of the above teachings. The embodiments described serve to explain the principles of the invention and its practical application and to enable others skilled in the art to utilize the invention in various embodiments and with various modifications as are suited to the particular use contemplated. Therefore, it is intended that the invention not be limited to the particular embodiments disclosed for carrying out the invention.

While particular embodiments of the present invention have been shown and described, it will be obvious to those skilled in the art that, based upon the teachings herein, changes and modifications may be made without departing from this invention and its broader aspects and, therefore, the appended claims are to encompass within their scope all such changes and modifications as are within the true spirit and scope of this invention. It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.).

What is claimed is:

1. A device for operating a microfluidic system comprising: one or more fluid interfacing components and a cartridge holder, wherein the one or more fluid interfacing components are fixed while the cartridge holder moves along a linear guide; wherein the one or more fluid interfacing components comprise one or more tubes, wherein the one or more tubes is capable of inserting into a cartridge provided in the cartridge holder, wherein the one or more tubes is fabricated of conductive material, and wherein the one or more tubes is electrically connected to a circuit board that is connected to a microprocessor, and wherein the one or more tubes is capable of providing electrical contact to fluid in a cartridge in the cartridge holder; and wherein one or more of the fluid interfacing components does not make direct contact with fluid in a cartridge provided in the cartridge holder; and wherein the device further comprises a means for making one or more electrical contacts to a cartridge in the cartridge holder.

2. The device of claim 1, further comprising a cartridge in the cartridge holder.

3. The device of claim 2, wherein the cartridge is reversibly engaged with one or more fluid interfacing components.

4. The device of claim 2, wherein the cartridge comprises one or more electrodes.

5. The device of claim 2, wherein the cartridge comprises electrodes that detect electrical signals generated when particles pass through a constriction in the cartridge.

6. The device of claim 5, wherein the constriction is a nano-sized constriction.

7. The device of claim 1, further comprising a locking system to avoid emission of fluid and/or gas when fluid and/or gas tubes are not engaged by a cartridge provided in the cartridge holder.

8. The device of claim 1, further comprising one or more of bias voltage contacts and one or more sense voltage contacts.

9. The device of claim 1, further comprising a means for electrical signaling to detect proper operation of the device.

10. The device of claim 1, wherein the device is a handheld device.

11. A method of analyzing a sample, comprising: providing the device of claim 1; and using the device to analyze the sample.

12. The method of claim 11, wherein the device further comprises a cartridge in the cartridge holder.

13. The method of claim 12, wherein the cartridge is reversibly engaged with one or more fluid interfacing components.

14. The method of claim 12, wherein the cartridge comprises electrodes.

15. The method of claim 12, wherein the cartridge comprises electrodes that detect electrical signals generated when particles pass through a constriction in the cartridge.

16. The method of claim 12, further comprising use of a pressure supply wherein the pressure supply controls the flow of fluid through different parts of the cartridge.

17. The method of claim 11, wherein the sample comprises micro-particles and/or nanoparticles.

18. The method of claim 11, further comprising use of a locking system to avoid emission of fluid and/or gas when fluid and/or gas tubes are not engaged by a cartridge provided in the cartridge holder.

19. The method of claim 11, further comprising use of one or more of bias voltage contacts and one or more sense voltage contacts.

20. The method of claim 11, further comprising use of electrical signaling to detect proper operation of the device.

21. The method of claim 11, wherein the sample is a biological sample.

22. The method of claim 21, wherein the biological sample includes virus and/or bacterium particles.

23. The method of claim 11, wherein the sample comprises one or more particles.

24. A method of diagnosing a disease in a subject, comprising: obtaining a sample from the subject; providing the device of claim 1; using the device to analyze the sample and determine the presence or absence of one or more markers associated with a disease; and diagnosing the disease in the subject based on the presence of the one or more markers.

25. The method of claim 24, wherein the marker is a biomarker.

26. The method of claim 24, wherein the sample is a biological sample.

27. The method of claim 24, wherein the subject is human.

28. The device of claim 1, wherein the device further comprises a single pressure maintaining unit.

29. The device of claim 28, wherein the device further comprises a single pressure supply, one or more pressure maintaining volumes, and electrically-controlled valves connecting the one or more pressure maintaining volumes to one or more fluid volumes in a cartridge in the cartridge holder.

30. The device of claim 1, wherein the one or more fluid interfacing components is rigid.

31. The device of claim 1, wherein the one or more tubes make individual electrical, fluidic and pneumatic contact with fluids in the cartridge.

32. The device of claim 1, wherein the one or more fluid interfacing components that does not make direct contact with fluid in a cartridge provided in the cartridge holder comprises a tube that is wider than the opening of a reservoir in the cartridge and forms a seal when pressed onto the cartridge.

33. The device of claim 1, wherein the means for making one or more electrical contacts to a cartridge in the cartridge holder comprises a spring connector on a circuit board.

* * * * *